(12) United States Patent
Rawat et al.

(10) Patent No.: US 8,619,002 B2
(45) Date of Patent: *Dec. 31, 2013

(54) RADIO FREQUENCY ANTENNA IN A HEADER OF AN IMPLANTABLE MEDICAL DEVICE

(75) Inventors: Prashant Rawat, Blaine, MN (US); Timothy Hillukka, Plymouth, MN (US); Jeffrey A. Von Arx, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 254 days.

This patent is subject to a terminal disclaimer.

(21) Appl. No.: 13/024,767

(22) Filed: Feb. 10, 2011

(65) Prior Publication Data

US 2011/0134013 A1  Jun. 9, 2011

Related U.S. Application Data

(63) Continuation of application No. 10/744,943, filed on Dec. 22, 2003, now Pat. No. 7,903,043.

(51) Int. Cl.
*H01Q 1/40* (2006.01)

(52) U.S. Cl.
USPC ............................. 343/873; 607/60; 343/872

(58) Field of Classification Search
USPC .............. 343/873; 600/302, 561, 398; 607/60
See application file for complete search history.

(56) References Cited

U.S. PATENT DOCUMENTS

| | | | |
|---|---|---|---|
| 4,441,498 A | 4/1984 | Nordling | |
| 4,519,401 A * | 5/1985 | Ko et al. | 600/561 |
| 4,542,532 A | 9/1985 | McQuilkin | |
| 4,542,535 A | 9/1985 | Bates et al. | |
| 4,562,841 A | 1/1986 | Brockway et al. | |
| 4,944,299 A | 7/1990 | Silvian | |
| 5,025,808 A | 6/1991 | Hafner | |
| 5,314,453 A | 5/1994 | Jeutter | |
| 5,342,408 A | 8/1994 | deCoriolis et al. | |
| 5,370,666 A | 12/1994 | Lindberg et al. | |
| 5,476,488 A | 12/1995 | Morgan et al. | |
| 5,579,876 A | 12/1996 | Adrian et al. | |
| 5,593,430 A | 1/1997 | Renger | |
| 5,598,847 A | 2/1997 | Renger | |
| 5,650,759 A | 7/1997 | Hittman et al. | |
| 5,683,432 A | 11/1997 | Goedeke et al. | |
| 5,697,958 A | 12/1997 | Paul et al. | |
| 5,752,977 A | 5/1998 | Grevious et al. | |
| 5,766,232 A | 6/1998 | Grevious et al. | |
| 5,807,397 A | 9/1998 | Barreras | |
| 5,843,139 A | 12/1998 | Goedeke et al. | |

(Continued)

OTHER PUBLICATIONS

"U.S. Appl. No. 10/744,943, Final Office Action mailed Feb. 21, 2008.", 15 pgs.

(Continued)

*Primary Examiner* — Jerome Jackson, Jr.
*Assistant Examiner* — Ricardo Magallanes
(74) *Attorney, Agent, or Firm* — Schwegman Lundberg & Woessner, P.A.

(57) ABSTRACT

An apparatus and method for enabling far-field radio frequency communications with an implantable medical device in which an antenna structure is disposed within a header assembly of the device. The antenna structure, in various embodiments, includes a monopole antenna, a dipole antenna, an inverted F antenna, a patch antenna and a slot antenna.

15 Claims, 8 Drawing Sheets

(56) References Cited

U.S. PATENT DOCUMENTS

| | | | |
|---|---|---|---|
| 5,861,019 A * | 1/1999 | Sun et al. ................. | 607/60 |
| 5,902,251 A * | 5/1999 | vanHooydonk ............ | 600/549 |
| 6,052,623 A * | 4/2000 | Fenner et al. ............. | 607/36 |
| 6,093,146 A | 7/2000 | Filangeri | |
| 6,115,583 A | 9/2000 | Brummer et al. | |
| 6,115,634 A | 9/2000 | Donders et al. | |
| 6,115,636 A | 9/2000 | Ryan | |
| 6,167,312 A | 12/2000 | Goedeke | |
| 6,169,925 B1 | 1/2001 | Villaseca et al. | |
| 6,240,317 B1 | 5/2001 | Villaseca et al. | |
| 6,249,700 B1 | 6/2001 | Alt | |
| 6,263,246 B1 | 7/2001 | Goedeke et al. | |
| 6,275,737 B1 | 8/2001 | Mann | |
| 6,309,350 B1 | 10/2001 | VanTassel et al. | |
| 6,329,920 B1 | 12/2001 | Morrison et al. | |
| 6,424,867 B1 | 7/2002 | Snell et al. | |
| 6,434,429 B1 | 8/2002 | Kraus et al. | |
| 6,443,891 B1 | 9/2002 | Grevious | |
| 6,456,256 B1 * | 9/2002 | Amundson et al. .......... | 343/873 |
| 6,470,215 B1 | 10/2002 | Kraus et al. | |
| 6,482,154 B1 | 11/2002 | Haubrich et al. | |
| 6,490,487 B1 | 12/2002 | Kraus et al. | |
| 6,505,072 B1 | 1/2003 | Linder et al. | |
| 6,527,729 B1 | 3/2003 | Turcott | |
| 6,531,982 B1 | 3/2003 | White et al. | |
| 6,564,104 B2 | 5/2003 | Nelson et al. | |
| 6,564,105 B2 | 5/2003 | Starkweather et al. | |
| 6,574,509 B1 | 6/2003 | Kraus et al. | |
| 6,574,510 B2 | 6/2003 | Von Arx et al. | |
| 6,577,900 B1 | 6/2003 | Silvian | |
| 6,577,901 B2 | 6/2003 | Thompson et al. | |
| 6,582,365 B1 | 6/2003 | Hines et al. | |
| 6,585,644 B2 | 7/2003 | Lebel et al. | |
| 6,600,949 B1 * | 7/2003 | Turcott ................. | 600/518 |
| 6,600,952 B1 | 7/2003 | Snell et al. | |
| 6,602,191 B2 | 8/2003 | Quy | |
| 6,609,029 B1 | 8/2003 | Mann et al. | |
| 6,614,406 B2 | 9/2003 | Amundson et al. | |
| 6,622,050 B2 | 9/2003 | Thompson | |
| 6,624,786 B2 | 9/2003 | Boyle | |
| 6,659,948 B2 | 12/2003 | Lebel et al. | |
| 6,662,048 B2 | 12/2003 | Balczewski et al. | |
| 6,675,045 B2 | 1/2004 | Mass et al. | |
| 6,687,546 B2 | 2/2004 | Lebel et al. | |
| 6,708,065 B2 | 3/2004 | Von Arx et al. | |
| 6,752,765 B1 | 6/2004 | Jensen et al. | |
| 6,804,559 B1 | 10/2004 | Kraus et al. | |
| 6,809,701 B2 | 10/2004 | Amundson et al. | |
| 6,873,870 B2 | 3/2005 | Ferek-Petric | |
| 6,951,596 B2 | 10/2005 | Green et al. | |
| 6,993,393 B2 | 1/2006 | Von Arx et al. | |
| 7,047,076 B1 | 5/2006 | Li et al. | |
| 7,069,086 B2 | 6/2006 | Von Arx | |
| 7,729,776 B2 | 6/2010 | Von Arx et al. | |
| 7,738,964 B2 | 6/2010 | Von Arx et al. | |
| 8,041,432 B2 | 10/2011 | Von Arx et al. | |
| 8,046,080 B2 | 10/2011 | Von Arx et al. | |
| 2001/0027331 A1 | 10/2001 | Thompson | |
| 2002/0013614 A1 | 1/2002 | Thompson | |
| 2002/0147388 A1 | 10/2002 | Mass et al. | |
| 2003/0018369 A1 | 1/2003 | Thompson et al. | |
| 2003/0028902 A1 | 2/2003 | Cubley et al. | |
| 2003/0114897 A1 | 6/2003 | Von Arx et al. | |
| 2003/0114898 A1 | 6/2003 | Von Arx et al. | |
| 2003/0149459 A1 | 8/2003 | Von Arx et al. | |
| 2003/0216793 A1 * | 11/2003 | Karlsson et al. ............. | 607/60 |
| 2004/0030260 A1 | 2/2004 | Arx | |
| 2004/0102815 A1 | 5/2004 | Balczewski et al. | |
| 2004/0215280 A1 | 10/2004 | Dublin et al. | |
| 2004/0236382 A1 | 11/2004 | Dinsmoor et al. | |
| 2004/0260363 A1 | 12/2004 | Arx et al. | |
| 2005/0134520 A1 | 6/2005 | Rawat et al. | |
| 2006/0116744 A1 | 6/2006 | Von Arx et al. | |
| 2010/0106224 A1 | 4/2010 | Von Arx et al. | |
| 2010/0152816 A1 | 6/2010 | Von Arx et al. | |

OTHER PUBLICATIONS

"U.S. Appl. No. 10/744,943, Non-Final Office Action mailed Mar. 19, 2010", 10 pgs.

"U.S. Appl. No. 10/744,943, Non-Final Office Action mailed Apr. 20, 2007", 8 pgs.

"U.S. Appl. No. 10/744,943, Non-Final Office Action mailed Aug. 1, 2006", 7 pgs.

"U.S. Appl. No. 10/744,943, Non-Final Office Action Mailed Aug. 7, 2009", 11 pgs.

"U.S. Appl. No. 10/744,943, Non-Final Office Action Mailed Oct. 28, 2008", 16 pgs.

"U.S. Appl. No. 10/744,943, Non-Final Office Action mailed Dec. 15, 2005", 7 pgs.

"U.S. Appl. No. 10/744,943, Notice of Allowance mailed Nov. 1, 2010", 7 pgs.

"U.S. Appl. No. 10/744,943, Response filed Feb. 1, 2007 to Non-Final Office Action mailed Aug. 1, 2006", 11 pgs.

"U.S. Appl. No. 10/744,943, Response filed Mar. 30, 2009 to Non-Final Office Action mailed Oct. 28, 2008", 8 pgs.

"U.S. Appl. No. 10/744,943, Response filed May 15, 2006 to Non-Final Office Action mailed Dec. 5, 2005", 9 pgs.

"U.S. Appl. No. 10/744,943, Response filed Aug. 18, 2010 to Non-Final Office Action mailed Mar. 19, 2010", 14 pgs.

"U.S. Appl. No. 10/744,943, Response filed Aug. 19, 2008 to Final Office Action mailed Feb. 21, 2008", 9 pgs.

"U.S. Appl. No. 10/744,943, Response filed Sep. 6, 2005 to Restriction Requirement mailed Aug. 3, 2005", 8 pgs.

"U.S. Appl. No. 10/744,943, Response filed Oct. 22, 2007 to Non-Final Office Action mailed Apr. 20, 2007", 9 pgs.

"U.S. Appl. No. 10/744,943, Response filed Nov. 9, 2009 to Non-Final Office Action mailed Aug. 7, 2009", 12 pgs.

"U.S. Appl. No. 10/744,943, Restriction Requirement mailed Aug. 3, 2005", 5 pgs.

"U.S. Appl. No. 11/325,584, Notice of Allowance mailed Mar. 23, 2010", 4 pgs.

"Japanese Application No. 2004-527861, Notice of Allowance mailed Jun. 16, 2010", 3 pgs.

Bange, Joseph E, et al., "U.S. Appl. No. 11/101,196, Application filed Apr. 7, 2005", 19 pgs.

Von Arx, Jeffrey, "U.S. Appl. No. 10/870,324, Application filed Jun. 14, 2004", 38 pgs.

* cited by examiner

RADIO FREQUENCY ANTENNA IN A HEADER OF AN IMPLANTABLE MEDICAL DEVICE

CLAIM OF PRIORITY

This application is a continuation of U.S. application Ser. No. 10/744,943, filed on Dec. 22, 2003, now issued as U.S. Pat. No. 7,903,043, the benefit of priority to which is claimed herein, and which is hereby incorporated herein by reference in its entirety.

CROSS-REFERENCE TO RELATED APPLICATIONS

This document is related to application Ser. No. 10/634,233, filed Aug. 5, 2003, now issued as U.S. Pat. No. 6,809,701, entitled CIRCUMFERENTIAL ANTENNA FOR AN IMPLANTABLE MEDICAL DEVICE, which is a continuation of application Ser. No. 10/252,494, now issued as U.S. Pat. No. 6,614,406, which is a continuation of application Ser. No. 09/921,653, now issued as U.S. Pat. No. 6,456,256, each of which are incorporated herein by reference.

This document is related to application Ser. No. 10/454,013, filed Jun. 3, 2003, now issued as U.S. Pat. No. 6,766,201, entitled TELEMETRY APPARATUS AND METHOD FOR AN IMPLANTABLE MEDICAL DEVICE which is a continuation of application Ser. No. 09/727,093, now issued as U.S. Pat. No. 6,574,510, each of which are incorporated herein by reference.

TECHNICAL FIELD

This subject matter pertains to implantable medical devices such as cardiac pacemakers and implantable cardioverter/defibrillators. In particular, the subject matter relates to an apparatus and method for enabling radio frequency telemetry in such devices.

BACKGROUND

Implantable medical devices, including cardiac rhythm management devices such as pacemakers and implantable cardioverter/defibrillators, usually have the capability to communicate data with a device called an external programmer via a radio frequency telemetry link. A clinician may use an external programmer to program the operating parameters of an implanted medical device. For example, the pacing mode and other operating characteristics of a pacemaker may be modified after implantation in this manner. Modern implantable devices also include the capability for bidirectional communication so that information can be transmitted to the programmer from the implanted device. Among the data which may be telemetered from an implantable device are various operating parameters and physiological data, the latter either collected in real-time or stored from previous monitoring operations.

Telemetry systems for implantable medical devices utilize radio frequency energy to enable bidirectional communication between the implantable device and an external programmer. A radio frequency carrier is modulated with digital information by, for example, amplitude shift keying where the presence or absence of pulses in the signal constitute binary symbols or bits. The external programmer transmits and receives the radio signal with an antenna incorporated into a wand which can be positioned in proximity to the implanted device. The implantable device also generates and receives the radio signal by means of an antenna formed by a wire coil wrapped around the periphery of the inside of the device casing.

In previous telemetry systems, the implantable device and the external programmer communicate by generating and sensing a modulated electromagnetic field in the near-field region with the antennas of the respective devices inductively coupled together. The wand must therefore be in close proximity to the implantable device, typically within a few inches, in order for communications to take place. This requirement is inconvenient for a clinician and limits the situations in which telemetry can take place.

SUMMARY

A radio frequency antenna assembly is disposed in a connector header of an implantable medical device. The connector header, also referred to as a header, is fabricated of an insulating material and the antenna assembly is fabricated of conductive material. In various embodiments, the antenna assembly includes a monopole antenna, a dipole antenna, an inverted F antenna, a patch antenna or a slot antenna. The effective dielectric constant seen by the antenna assembly is selected to meet a particular transmission performance measure by coating the antenna conductor and by embedding the antenna in a cavity filled with a material having a predetermined dielectric constant.

In addition to housing the antenna assembly, the header also provides electrical connections for leads or other circuits of the implantable device. The header assembly is affixed to the medical device by an adhesive or mechanical fasteners.

Other aspects will be apparent on reading the following detailed description and viewing the drawings that form a part thereof.

DETAILED DESCRIPTION

Figure 1A:
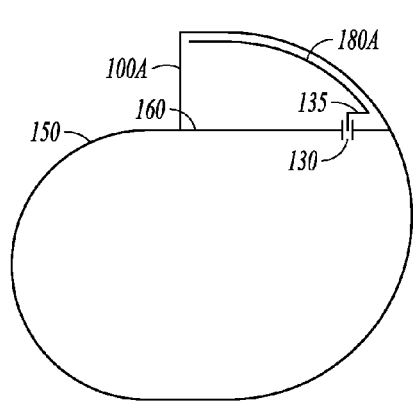
FIGS. 1A, 1B, 1C and 1D schematically illustrate various antenna configurations disposed in a header of an implantable device.

In the following detailed description, reference is made to the accompanying drawings that form a part hereof, and in which is shown, by way of illustration, specific embodiments in which the present subject matter may be practiced. These embodiments are described in sufficient detail to enable those skilled in the art to practice the subject matter, and it is to be understood that the embodiments may be combined, or that other embodiments may be utilized and that structural, mechanical, logical and electrical changes may be made without departing from the scope of the present subject matter. The following detailed description is, therefore, not to be taken in a limiting sense, and the scope of the present subject matter is defined by the appended claims and their equivalents.

As noted above, conventional radio frequency (RF) telemetry systems used for implantable medical devices such as cardiac pacemakers utilize inductive coupling between the antennas of the implantable device and an external programmer in order to transmit and receive radio frequency signals. Because the induction field produced by a transmitting antenna falls off rapidly with distance, such systems require close proximity between the implantable device and a wand antenna of the external programmer in order to work properly, usually on the order of a few inches.

The present subject matter, on the other hand, includes an apparatus and method for enabling telemetry with an implantable medical device utilizing far-field radiation. Communication using far-field radiation can take place over much greater distances which makes it more convenient to use an external, or remote, programmer. Also, the increased communication range makes possible other applications of the telemetry system such as remote monitoring of patients and communication with other types of external devices.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the radio frequency energy used to drive an antenna is such that the wavelength of electromagnetic waves propagating therein is much greater than the length of the antenna, a negligible far-field component is produced. In order for a substantial portion of the energy delivered to the antenna to be emitted as far-field radiation, the wavelength of the driving signal should not be very much larger than the length of the antenna.

An antenna most efficiently radiates energy if the length of the antenna is an integral number of half-wavelengths of the driving signal. A dipole antenna, for example, is a center-driven conductor that has a length equal to half the wavelength of the driving signal. Such a dipole antenna can be made, for example, of two lengths of metal arranged end to end with the cable from a transceiver coupled to each length of the dipole in the middle. An efficiently radiating resonant structure is formed if each length of metal in the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field.

A monopole antenna includes a conductor with a length equal to one-quarter the wavelength of the driving signal situated with respect to a reflecting ground plane so that the total emitted and reflected field configuration resembles that of the dipole antenna. For implantable medical device applications, the carrier frequency is typically between 300 MHz and 1 GHz however frequencies less than 300 MHz or greater than 1 GHz are also contemplated. By way of example, for a carrier signal of 1 GHz, the wavelength in free space is approximately 32 cm. In free space, a half-wavelength dipole antenna would optimally be approximately 16 cm long, and a quarter-wavelength monopole antenna would optimally have a length approximately 8 cm with the housing, or other conductive surface, serving as a ground plane. Because the permittivity of body tissues is greater than that of free space, the corresponding optimum dipole and monopole antennas in the human body would be approximately half these lengths. A longer antenna length is used for a lower frequency carrier.

In addition to the resonant frequency, antennas are also characterized by a quality, or Q factor and an impedance. The Q of an antenna is a measure of performance or quality of a resonator and is a function of the measure of energy loss or dissipation per cycle as compared to the energy stored in the fields inside the resonator. Antenna impedance is the sum of a real component and an imaginary component. In one embodiment, the antenna of the present subject matter presents an impedance between approximately 35 and 150 ohms, however lower or higher impedances area also contemplated.

In one embodiment, the device housing is metallic and forms an electrically shielded compartment for electronic circuitry that provides particular functionality to the device such as cardiac rhythm management, physiological monitoring, drug delivery, cardiac therapy, or neuromuscular stimulation. The housing also contains electronic circuitry for transmitting and receiving radio frequency communications. In one embodiment, the device housing includes a synthetic polymer and a portion of the housing includes a conductive surface which functions as a ground plane.

The antenna includes a conductor disposed within the header, or on a surface of the header. The antenna, in various embodiments is insulated or uninsulated, and is electrically connected to a radio frequency circuit within the housing. The antenna includes a conductive structure capable of radiating electromagnetic energy such as a rod, a wire, a planar conductor, a patch, a slot or a loop. A wire antenna, for example, is simple to manufacture and is volumetrically efficient. A wire antenna also tends to have a near isotropic radiation pattern in the horizontal plane with fewer null locations as compared with other types of antennas. A near isotropic radiation pattern is particularly desirable with a far-field telemetry system in an implantable device since movement of the user may arbitrarily orient the antenna with respect to the receiving antenna of the external device. In one embodiment, the antenna includes a flexible or rigid ribbon conductor.

In one embodiment, the antenna is fabricated of metal wire such as, for example, an alloy of platinum and iridium. In one embodiment, the alloy includes approximately 90% platinum and 10% iridium. Such a material is commonly used for feedthroughs of therapeutic leads and is both mechanically strong and biocompatible. In one embodiment, the antenna is integrated with the feedthrough conductor and, as such, no welding or other means of attachment is required for attaching the antenna to the device and the antenna can be routed from the electronic circuitry within the housing, through the feedthrough, and to the header with no interposing connections required. In one embodiment, the antenna and feedthrough material includes niobium, which has a slightly lower resistivity than the 90% platinum and 10% iridium alloy. Other materials for the antenna are also contemplated, including, but not limited to, stainless steel, gold, silver and other conductors having low resistance and which are biocompatible.

In accordance with one embodiment of the present subject matter, the antenna is disposed in the header of the implantable medical device. The header provides a connection to the device for therapy leads external to the housing, an antenna and other components.

In one embodiment, the header is fabricated of insulative material, such as polyurethane resin, having a particular dielectric constant. In one embodiment, the header is fabricated of a thermoplastic urethane. For example, Tecothane® (Thermedics Inc., Woburn, Mass.) is an aromatic polyether-based thermoplastic polyurethane which has a dielectric constant of about 4.4. For a header fabricated of Tecothane®, the capacitance is approximately four times greater than would be the case if the antenna and header were separated by air. High capacitance may result in unacceptable losses to the antenna. A material with a lower dielectric constant of only 2.1 to 2.4 is polytetrafluoroethylene (PTFE). A header fabricated of PTFE rather than thermoplastic urethane increases the radiation efficiency of the antenna by decreasing the capacitance between the antenna and the device housing. Absorption of water by the header also increases the dielectric constant, and PTFE is hydrophobic while Tecothane® is hydrophilic. Other materials with lower dielectric constants suitable for use as a header material include expanded polytetrafluoroethylene (ETFE) with a dielectric constant of 2.6, and polyetheretherketone (PEEK) with dielectric constant of 3.6.

A particular embodiment of the present subject matter that minimizes space requirements but still allows for efficient radiation includes a wire antenna embedded within a header of the device. In various embodiments, a wire antenna is disposed in substantially parallel alignment with a curved surface of the header or the antenna is aligned in a linear manner. As used herein, substantially parallel includes routing of the antenna such that, over at least a portion of the length of the antenna, the surface of the header and the antenna are conformal. If the wire antenna is positioned a fixed distance from a conductive surface of the housing, the wire exhibits radiation characteristics between a transmission line and a monopole antenna. If the wire diameter is small and the separation between the wire and the conductive surface of the housing is reasonably distant, the wire thus acts as a transmission line antenna. The antenna is thus a one-piece design integral to the implantable device and permits the antenna to have a longer electrical length.

Given the physical constraints associated with placement of an antenna within a header of implantable devices, an ideal monopole antenna may not be practical at the desired carrier frequency. A lossy transmission line, however, can be made to have radiation characteristics that resemble the performance of a monopole antenna. Although such a transmission line antenna may not be as efficient as a quarter-wavelength monopole, it does offer a balanced compromise between size, efficiency, and radiation pattern.

FIGS. 1A, 1B, 1C and 1D show different embodiments of exemplary implantable device, each with an antenna in header 100A suitable for radiating and receiving far-field electromagnetic radiation. The device housing 150 includes metallic surface 160 and contains electronic circuitry (not shown) for providing particular functionality to the device such as, for example, cardiac rhythm management, physiological monitoring, drug delivery, or neuromuscular stimulation as well as circuitry for providing radio frequency communications. In one embodiment, housing 150 includes a conductive metallic structure, such as titanium and surface 160 includes a particular portion of housing 150. In one embodiment, housing 150 includes a case fabricated of non-conductive material as well as a conductive film or foil to serve as a ground plane. In each of the figures, feedthrough 130 provides an electrical connection to a feed line coupled to the antenna. Feedthrough 130 provides an electrically isolated conductive path through a wall of housing 150 and also provides a hermetic seal for the environment within the interior of housing 150.

In FIG. 1A, antenna 180A includes a monopole antenna disposed to conform to a surface of header 100A. Antenna 180A is positioned below a surface of header 100A at a depth selected to provide physical protection from externalities as well as to provide a region surrounding antenna 180A having sufficient width to provide a particular dielectric constant value. The dielectric constant value for tissue and organs is not readily controllable or predictable. Thus, by disposing antenna 180A within a region having a known dielectric constant, the performance of antenna 180A is predictable. Feed line 135 couples antenna 180A to an electric circuit within housing 150 via feedthrough 130.

Figure 1B:
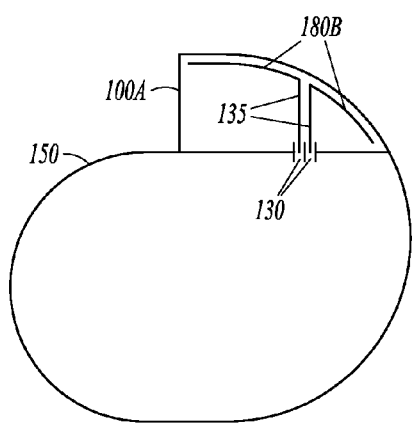

In FIG. 1B, antenna 180B includes a dipole antenna disposed to conform to a surface of header 100A. Dipole antenna 180B includes two feed lines 135, each of which are coupled to an electric circuit within housing 150 via feedthroughs 130. Unlike the monopole antenna 180A, dipole antenna 180B does not require a ground plane, and thus, surface 160 is not provided in the figure. Dipole antenna 180B includes two feedthroughs 130 and is tuned by adjusting the lengths of each antenna segment.

Figure 1C:
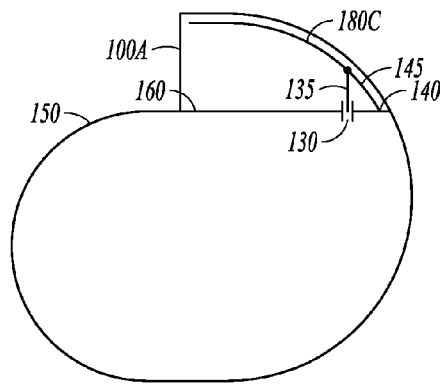

In FIG. 1C, antenna 180C includes an inverted F antenna disposed within header 100A and adapted to conform to a surface of header 100A. Feed line 135 of antenna 180C is coupled to an electric circuit within housing 150 via feedthrough 130. In addition, antenna 180C includes shunt 145 coupled to surface 160 at connection 140 as well as a portion of antenna 180C. Surface 160 is also coupled to the electric circuit within housing 150. Surface 160 functions as a ground plane for antenna 180C.

Figure 1D:
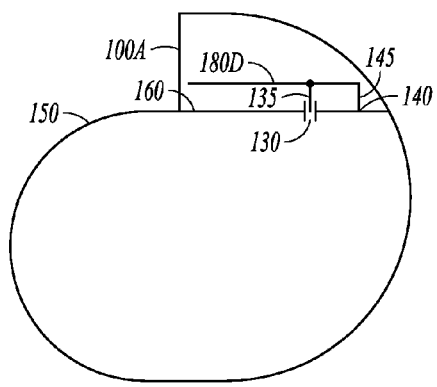

In FIG. 1D, antenna 180D includes an inverted F antenna disposed within header 100A. Antenna 180D includes a linear conductor segment and is not configured to conform to a surface of header 100A. As with antenna 180C, feed line 135 is coupled to an electric circuit within housing 150 via feedthrough 130 and antenna 180D is coupled to connection 140 on surface 160 by shunt 145. Surface 160 functions as a ground plane for antenna 180D and is also electrically coupled to the electric circuit within housing 150.

Figure 2A:
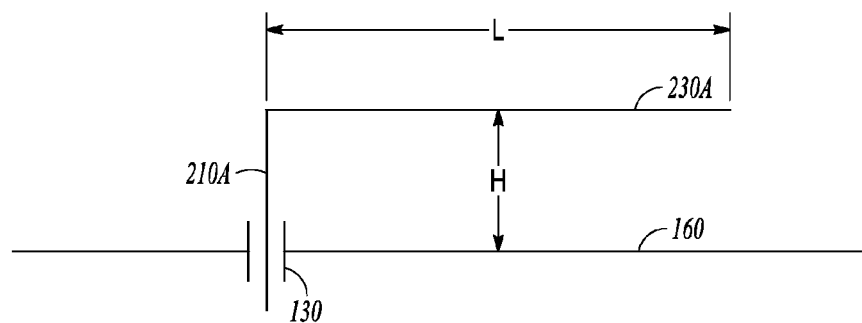
FIGS. 2A and 2B illustrate electrical schematics for selected antenna configurations.
Figure 2B:
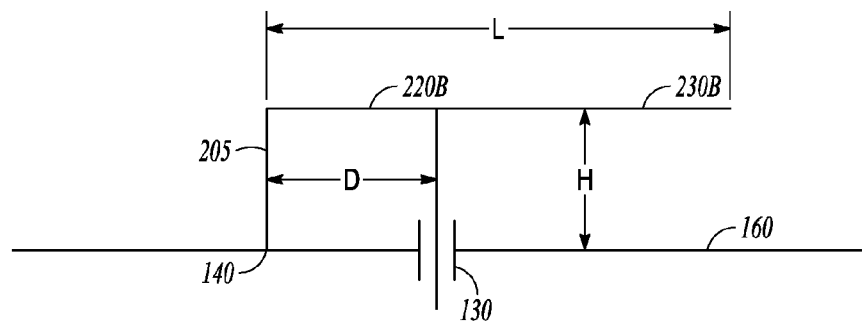

FIGS. 2A and 2B schematically illustrate a monopole and inverted F antenna, respectively. In the figures, feed lines 210A and 210B, respectively, pass through a wall of the housing at feedthrough 130 and are connected to an electrical circuit (not shown) within the housing. Surface 160, in various embodiments, is a conductive surface of the housing or represents a portion of a conductive housing and serves as a ground plane. Surface 160 is electrically coupled to the electric circuit within the housing.

In FIG. 2A, antenna 230A includes a monopole antenna. Radio frequency energy is emitted at a far field relative to the antenna. The length of antenna 230A, represented by dimension L, is selected for transmission and reception efficiency. For efficiency, dimension L is a function of the carrier frequency used for radio frequency communications. Dimension H affects the impedance presented by antenna 230A and is also selected for communication efficiency. In one embodiment, dimension L is maximized to improve reception.

In FIG. 2B, feed line 210B, conductive segments 220B and 230B and shunt 205 form an inverted F antenna. As with the monopole antenna of FIG. 2A, radio frequency energy is emitted at a far field relative to the inverted F antenna of FIG. 2B. Dimensions D, L and H are selected for communication efficiency and are a function of the carrier frequency. In one embodiment, dimension D is adjusted to change the resonant frequency of the antenna. Dimension H for an inverted F antenna is generally shorter than that of a comparable monopole antenna. In one embodiment, shunt 205 is electrically coupled to surface 160 by a soldered or welded joint.

Figure 3A:
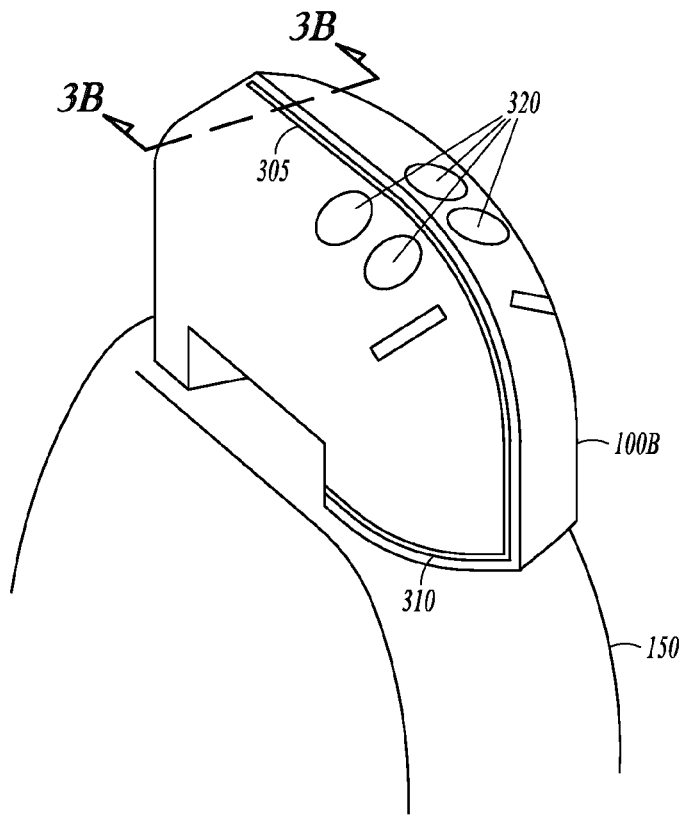
FIG. 3A includes a perspective view of a header coupled to an implantable device.

FIG. 3A illustrates a perspective view of an antenna disposed in header 100B. Header 100B is coupled to a surface of housing 150. Header 100B, in one embodiment, includes a molded polymer such as thermoplastic polyurethane. An electrical connection between a therapy lead or other electrical lead is established by inserting an end into a lead connector (not shown) on a surface of header 100B. For each electrical lead, a lead clamp 320 is disposed on another surface of header 100B. In one embodiment, lead clamp 320 includes a set screw with a protective cover. In the embodiment illustrated, header 100B is configured to receive four electrical leads, each having clamp 320, however, more or less than four leads are also contemplated.

Figure 3B:
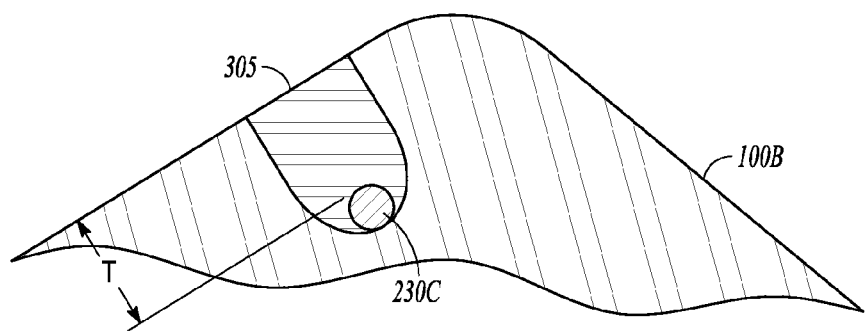
FIG. 3B includes a sectional view of a header with an antenna in a silicone filled trench.

In FIG. 3A, an antenna is disposed beneath overlay 305 in a surface of header 100B and a feed line is disposed beneath overlay 310 in a surface of header 100B. A sectional view of a header with a trench is illustrated in FIG. 3B. Header 100B includes a groove, or trench in an external surface. The trench is formed by molding or by a materials removal process subsequent to molding. In the figure, antenna conductor segment 230C is placed within the trench. Overlay 305 represents an encapsulating material disposed in the trench. In one embodiment, the encapsulating material includes silicone or other material suitable for implantation. The encapsulating material provides physical protection for the antenna and provides a suitable and predictable dielectric constant for the antenna. The antenna is embedded below a surface of header 100B by a depth denoted as dimension T. Dimension T, in one embodiment, is greater than approximately 10 mils, however, greater or smaller dimensions of depth below the surface are also contemplated. The depth of the trench is sufficient to receive the antenna and provide an encapsulating material depth of dimension T or greater. In one embodiment, a silicone overlay is applied over an antenna disposed in a trench.

Overlay 310 of FIG. 3A, in one embodiment, includes an encapsulating material in a groove and provides a conduit for a feed line supplying a radio frequency signal to the antenna and for supplying a received signal from the antenna to an electrical circuit.

In one embodiment, the antenna is assembled in a header and an overmold assembly is affixed to the header to provide a protective outer shell having a specified dielectric constant.

In one embodiment, the antenna is positioned within the header such that deleterious loading effects of nearby conductors is reduced. For example, an electrical therapy lead, a lead bore hole, or other conductive structure, located adjacent to the antenna will alter the radiation pattern transmitted by the antenna. In one embodiment, the antenna is positioned within the header at a distance no closer than approximately 25 mils from a conductor that is electrically isolated from the antenna.

Capacitance of the antenna may result in losses that reduce the radiation efficiency. These losses become larger as the frequency of the driving signal increases and as the capacitance increases. One way to decrease the value of the capacitance is to increase the distance separating the antenna from the device housing. The capacitance resulting from the proximity of the antenna and the conductive surface 160 is a function of the dielectric constant of the header, the physical separation and the carrier frequency. In one embodiment, the separation distance between the antenna and surface 160 is on the order of 1.5 to 2.5 millimeters. Capacitance can be reduced, for example, by selection of a header material having a lower dielectric constant.

Reducing the capacitive loading of an antenna, however, also decreases its effective electrical length, thus compromising the ability to operate at lower frequencies. In order to increase capacitive loading, in one embodiment, the antenna is coated with a film of high dielectric material. The film, in various embodiments, includes an oxide such as titanium oxide, aluminum oxide and barium strontium titanate. The film provides a uniformly high dielectric constant as seen by the antenna. The film can be formed, for example but not by way of limitation, by deposition of films and coatings, film growth or epitaxy, including for example, deposition by sputtering, vacuum deposition, laser deposition, chemical vapor deposition, molecular epitaxy, atomic epitaxy, ion epitaxy, chemical beam epitaxy, ion and electron beam-assisted deposition, ion plating, electrodeposition, electroplating and spray coating. In one embodiment, the antenna includes a conductive material in the form of a wire or rod. Other antenna configurations are also contemplated, including for example, planer material such as foil, sheet goods, or other conductive surfaces formed by semiconductor fabrication techniques using a substrate.

Figure 4A:
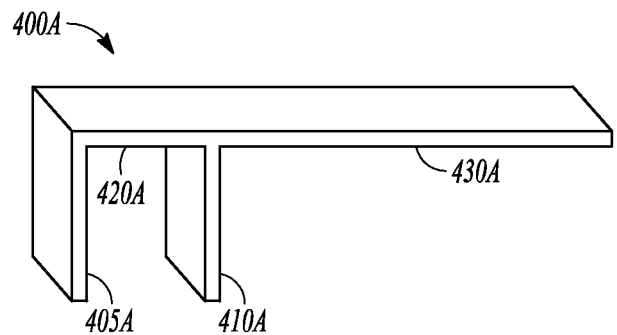
FIGS. 4A, 4B and 4C illustrate alternative embodiments for antennas according to one embodiment of the present subject matter.
Figure 4B:
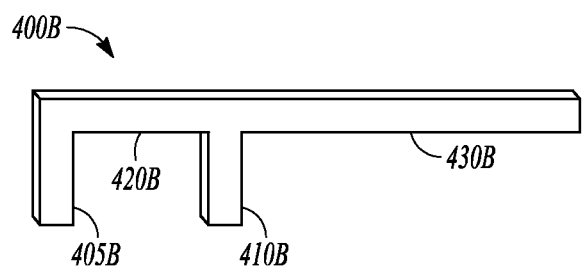
Figure 4C:
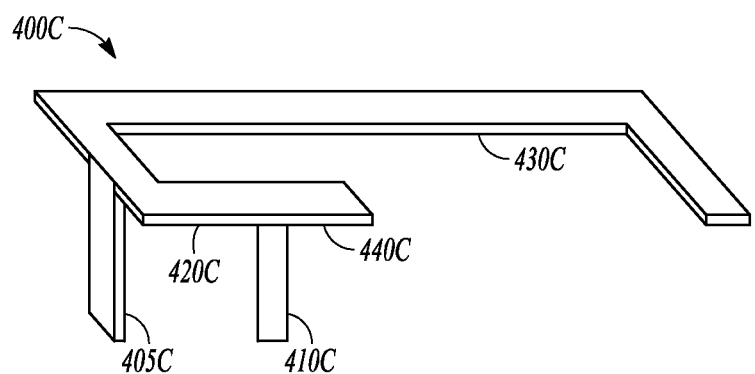

FIGS. 4A, 4B and 4C illustrate various representative configurations for an antenna structure. In particular, the figures illustrate variations of an inverted F antenna fabricated using flat conductive material, however, it is understood that these, and other configurations, such as monopole and dipole antennas, are also contemplated. In addition to the flat conductive materials or foil structures illustrated herein, an inverted F antenna can also be fabricated using, for example, wire or rod-type materials as well.

FIG. 4A illustrates antenna 400A fabricated of flat conductive material, such as foil having been formed by bending or other machining operation. Feed line 410A is coupled to an electric circuit within an implanted housing and shunt 405A is coupled to a ground plane, such as surface 160. Segment 420A has a length, as denoted by dimension D in FIG. 2B, selected to tune the antenna to a particular frequency. The effective antenna length is the combined length of segment 420A and 430A.

FIG. 4B illustrates antenna 400B fabricated of planar conductive material. In one embodiment, antenna 400B is fabricated by etching or other material removal process and requires no bending of structures. In one embodiment, antenna 400B is fabricated using photolithography or other semiconductor fabrication processes. Feed line 410B is coupled to an electric circuit within the housing and shunt 405B is coupled to a ground plane. The length of segment 420B can be adjusted by etching a particular side of feed line 410B. For example, the length of segment 420B increases by etching, or otherwise removing a portion of, the left side of feed line 410B. In addition, the length of segment 430B increases by etching, or otherwise removing a portion of, the right side of feed line 410B.

Each of antennas 400A and 400B have a single resonant frequency at which the antenna is tuned. In contrast, FIG. 4C illustrates antenna 400C having dual resonant frequencies. Thus, antenna 400C can be operated at either a first resonant frequency or at a second resonant frequency. For example, when the implantable device is located in a first geographical location (such as in a first country), the antenna is operated at a first resonant frequency and when the device is located in a second location (such as in a second country), the antenna is operated at a second resonant frequency. In FIG. 4C, antenna 400C includes feed line 410C and shunt 405C. The two resonant frequencies of antenna 400C are determined by the effective lengths of segments 440C, 420C, and 430C. In other embodiments, the header includes an antenna having more than two resonant frequencies. Antenna 400C, in one embodiment is configured to conform to a profile of an exterior surface of a header, as shown, for example, in FIG. 1C. Placement of antenna 400C in parallel with a surface of a header allows greater clearance between antenna 400C and other conductive surfaces. The dual resonant frequency antenna of FIG. 4C is but one example and other antenna structures having different geometrical configurations are also contemplated.

Figure 5:
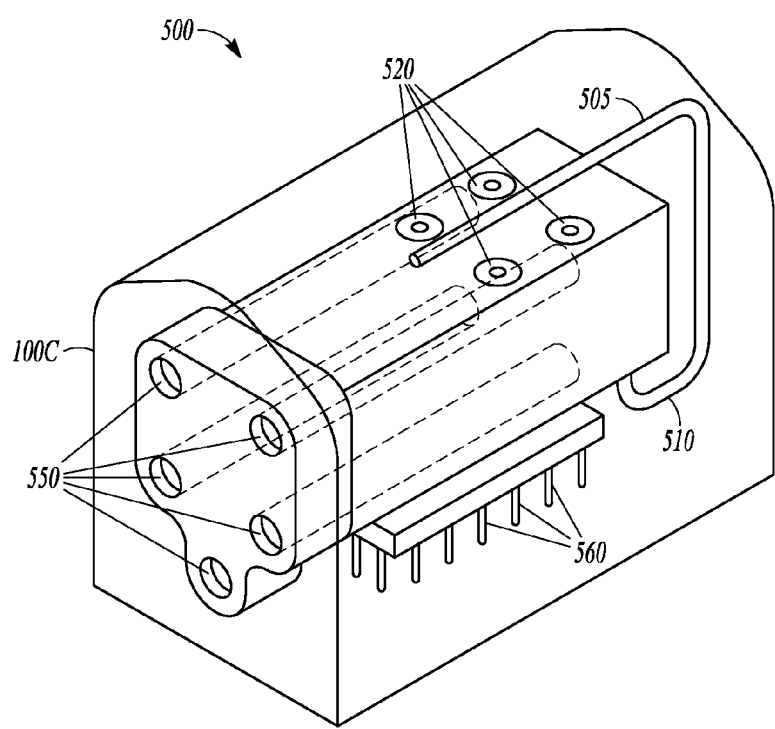
FIG. 5 includes a perspective view of an antenna in a transparent header.

FIG. 5 is a perspective view of header assembly 500 including antenna 505 in header 100C, shown to be transparent. In one embodiment, header 100C is opaque. In the figure, antenna 505 includes a monopole antenna structure having feed line 510. Header 100C includes connector block 555 having five electrical lead connectors 550. Clamps 520 are disposed on an upper surface of connector block 555 and each includes a clamp screw or other structure to secure an electrical lead in a connector 550. Electrical connector pins 560 are disposed on a lower surface of header assembly 500 and provide electrical connections with the implantable medical device (not shown).

Antenna 505 and feed line 510 are disposed in a bore or cavity within header 100C. In one embodiment the bore is filled with an encapsulating material such as silicone. In one embodiment, header 100C is fabricated in two or more discrete pre-molded sections to facilitate assembly of antenna 505 and feed line 510 therein. Antenna 550 is positioned within header 100C such that lead connectors, and other conductive surfaces, are no closer than approximately 25 mils.

Figure 6A:
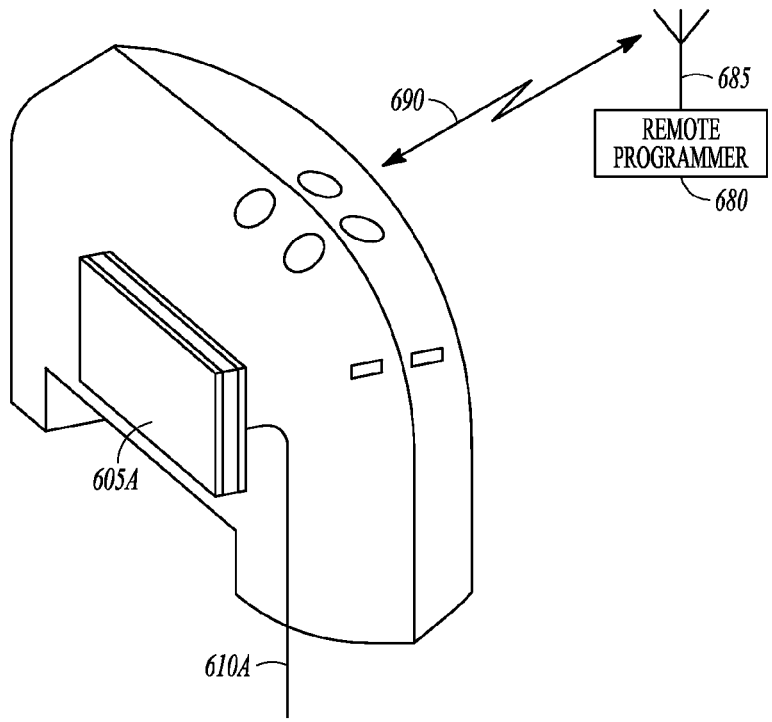
FIG. 6A includes a patch antenna in a header in communication with a remote programmer.

FIG. 6A includes a perspective view of patch antenna 605A within header 100C. Header 100C is shown to be transparent. In the figure, patch antenna 605A is molded, or otherwise disposed, on or below a single surface of header 100C however, it will be understood that the header can be configured with a segmented patch antennas with each antenna segment distributed on one or more surfaces of header 100C. Feed line 610A is coupled to antenna 605A and is coupled to an electronic circuit within a housing (not shown). In one embodiment, patch antenna 605A includes a laminated structure of dielectric material sandwiched between conductive material. In one embodiment, the dielectric material includes a thermoplastic polyurethane (such as Tecothane®), a ceramic substrate or a printed circuit board (such as FR4), and the conductive material includes metallic foils or films. FR4 is a laminate made of woven fibreglass fabric saturated with an epoxy resin and can be used in both double sided materials and multilayer base materials.

FIG. 6A also includes remote programmer 680 coupled to antenna 685. Remote programmer 680 includes a transceiver compatible with the transceiver of the implantable device and which communicates over far field radio frequency link 690. In one embodiment, both remote programmer 680 and a housing (not shown) coupled to header 100C includes transceivers. Other configurations are also contemplated, including, for example, a transmitter in the implantable device and a receiver in the remote programmer as well as a transmitter in the remote programmer and a receiver in the implantable device.

Figure 6B:
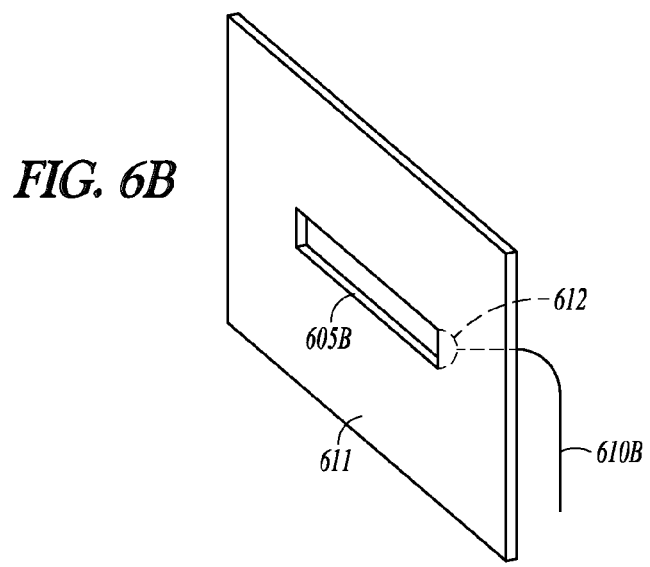
FIG. 6B includes a slot antenna according to one embodiment of the present subject matter.

FIG. 6B includes a slot antenna according to one embodiment of the present subject matter. In the embodiment illustrated, slot antenna 605B includes an elongate opening in conductive sheet 611. Feed point 612 is shown in hidden lines and bonds feed line 610B to slot antenna 605B. Other configurations of feeding slot antenna 605B with feed line 610B are also contemplated, including for example, but not by way of limitation, a feed at an edge of the slot or a feed in the same plane as the slot or a feed perpendicular to the surface of sheet 611. In addition, other slot configurations are also contemplated. In operation, a standing wave is generated inside the aperture or slot and radiation occurs due to the aperture.

Figure 7:
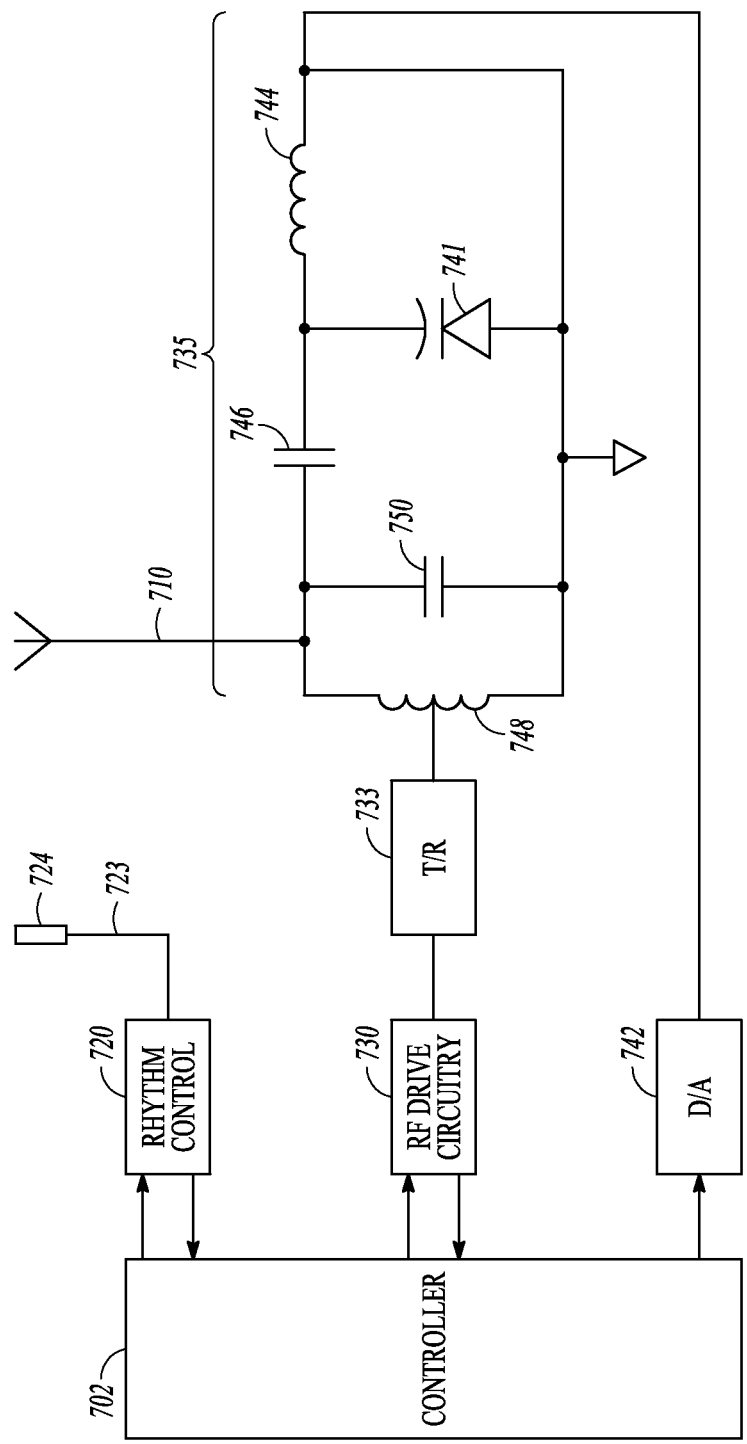
FIG. 7 includes an electrical schematic according to one embodiment of the present subject matter.

FIG. 7 includes a block diagram of an electrical circuit in an implantable medical device, some portions of which are disposed in the header of the device and some portions of which are disposed in the housing of the device. The circuit of FIG. 7 is powered by a power supply, such as a battery or other storage device, which is omitted from the figure for clarity. The circuit of FIG. 7, in one embodiment, represents a cardiac rhythm management device in which the present subject matter is used as a radio frequency antenna. The device includes a conductive housing (not shown) and is typically made of metal, such as for example, titanium. The housing includes one or more feedthroughs for establishing an electrical connection to selected components internal to the housing.

In the figure, therapy lead 723 is shown coupled to electrode 724, however, it is understood that an implantable medical device may include more than one such lead or electrode. Therapy lead 723 is connected to the circuit within the housing by a header.

Controller 702 controls the operation of rhythm control circuitry 720. Controller 702, in one embodiment, includes a microprocessor. Rhythm control circuitry 720 includes sensing and stimulus generation circuitry that are connected to electrode 724 by therapy lead 723. The conductors of therapy lead 723 are connected to rhythm control circuitry 720. Rhythm control circuitry 720, in various embodiments, includes at least one of any combination of a therapy circuit and a monitoring circuit.

Radio frequency drive circuitry 730 includes a radio frequency transmitter and receiver (a transceiver) that are connected by T/R switch 733 to antenna 710. Switch 733 is selectively operated to provide both transmit and receive functions. Controller 702 outputs and receives the data contained in the modulated carrier generated or received by radio frequency drive circuitry 730.

In one embodiment, radio frequency drive circuitry 730 is connected to antenna 710 through antenna tuning circuit 735. Antenna tuning circuit 735 loads antenna 710 with a variable amount of inductance or capacitance to thereby adjust, or tune, the effective electrical length of antenna 710.

In this manner, the reactance of antenna 710 can be tuned out so that antenna 710 forms a resonant structure at the specified carrier frequency and efficiently transmits and receives far-field radiation. Antenna tuning circuit 735 in the embodiment shown, includes a radio frequency matching circuit made up of inductor 748 and capacitor 750. A variable amount of capacitance is added to the matching circuit by varactor diode 741 which is controlled by a tuning bias voltage provided by digital-to-analog converter 742. Radio frequency choke filter 744 isolates digital-to-analog converter 742 from the radio frequency circuitry while allowing it to set the DC voltage of varactor diode 741. A DC blocking capacitor 746 isolates the radio frequency circuitry from the DC voltage across the varactor diode. By adjusting the voltage of varactor diode 741, antenna 710 can be tuned to various carrier frequencies under control of controller 702. This makes it possible to use various antenna structures of different dimensions at a specified carrier frequency as well as to efficiently radiate energy at a wide range of frequencies. Examples of antenna structures with which the tuning circuit can be used include antennas disposed within a non-conductive portion of the header and patch antennas disposed in the header.

In one embodiment, the antenna is coupled to a radio frequency circuit having a non-adjustable matching circuit. The antenna is sized to match the impedance of the matching circuit and no programmable or manual adjustments are provided.

Figure 8:
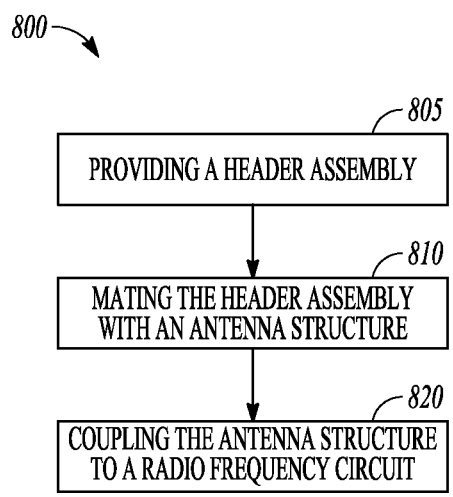
FIG. 8 includes a flow chart of a method according to one embodiment of the present subject matter.

FIG. 8 includes a flow chart of method 800 according to one embodiment of the present subject matter. At 805, a header assembly is provided. The header assembly is adapted for attachment to a housing of an implantable medical device. The header assembly provides electrical connections for electrical leads and a radio frequency circuit of the device. At 810, the header assembly and an antenna structure are mated together. In one embodiment, mating includes placing the antenna structure in a trench and filling the trench with an encapsulating material. In one embodiment, mating includes inserting an antenna structure in a bore of the header assembly. At 820, the antenna structure is electrically coupled to the radio frequency circuit of the implantable medical device. In one embodiment, this includes attaching the header assembly to the device housing.

Alternative Embodiments

In one embodiment, multiple antennas are provided in a single header. For example, a first antenna supports radio frequency communications at a first carrier frequency and a second antenna supports radio frequency communications at a second carrier frequency. As another example, in one embodiment, a first antenna is tailored to receive radio frequency communications and a second antenna is tailored to transmit radio frequency communications. Other configurations of multiple antennas are also contemplated.

In one embodiment, an antenna is disposed on an external surface of the header assembly. The antenna includes any combination of at least one of a monopole antenna, a dipole antenna, an inverted F antenna, a patch antenna and a slot antenna. In one embodiment, a protective coating is applied atop the antenna to provide physical protection for a conductive element of the antenna structure.

CONCLUSION

The above description is intended to be illustrative, and not restrictive. Many other embodiments will be apparent to those of skill in the art upon reviewing the above description.

What is claimed is:

1. An apparatus comprising: a header assembly for an implantable medical device, the header assembly configured to provide an electrical connection for a lead extending away from the header assembly, comprising: an antenna configured to be coupled to an electronic circuit within a housing of the implantable medical device, the electronic circuit configured for radio frequency communication using the antenna; and a dielectric material comprising one or more of polytetrafluoroethylene, expanded polytetrafluoroethylene, polyetheretherketone, or a thermoplastic polyurethane, the dielectric material configured to isolate the antenna from tissue of a patient when the header assembly is implanted in the patient, and to dispose at least a portion of the antenna within the dielectric material at a specified distance from a surface of the header assembly, the dielectric material comprising a trench filled with a silicone material when the antenna is positioned within the trench, the trench configured to retain at least a portion of the antenna at a specified depth from the surface of the header assembly.

2. The apparatus of claim 1, wherein the antenna comprises an inverted-F configuration including a conductor located parallel to the surface of the header assembly at a specified distance from the surface of the header assembly.

3. The apparatus of claim 2, wherein at least a portion of the conductor comprises a planar conductor.

4. The apparatus of claim 1, wherein a long axis of the antenna is located parallel to the surface of the header assembly at a specified distance from the surface of the header assembly.

5. The apparatus of claim 1, wherein the antenna comprises a conductor configured to be coupled to the electronic circuit, the conductor configured to pass through a feedthrough assembly located along a housing of an implantable medical device, and the electronic circuit located within the housing.

6. The apparatus of claim 1, wherein the antenna comprises a wire including a platinum-iridium alloy.

7. The apparatus of claim 1, wherein the antenna includes an oxide coating.

8. The apparatus of claim 1, wherein the antenna comprises a conductor located on a ceramic substrate within the dielectric material of the header assembly.

9. The apparatus of claim 1, wherein the antenna is configured to provide a first resonance corresponding to a first desired operating frequency range for radio frequency communication, and a second resonance corresponding to a different second desired operating frequency range, for radio frequency communication using one or more of the first range or the second range.

10. The apparatus of claim 1, comprising the implantable medical device, including: the housing including the electronic circuit configured for radio frequency communication; the header assembly, coupled to the housing; and the antenna.

11. The apparatus of claim 10, further comprising an implantable lead assembly; and wherein the header is configured to provide one or more electrical interconnections between one or more conductors included as a portion of the implantable lead and the electronic circuit.

12. An apparatus comprising: a header assembly for an implantable medical device, the header assembly configured to provide an electrical connection for a lead extending away from the header assembly, the header assembly comprising: an antenna configured to be coupled to an electronic circuit within a housing of the implantable medical device, the electronic circuit configured for radio frequency communication using the antenna; and a dielectric material comprising one or more of polytetrafluoroethylene, expanded polytetrafluoroethylene, polyetheretherketone, or a thermoplastic polyurethane, the dielectric material configured to isolate the antenna from tissue of a patient when the header assembly is implanted in the patient, and configured to dispose at least a portion of the antenna within the dielectric material at a specified distance from a surface of the header assembly to load the antenna with a specified dielectric constant, the dielectric material comprising a trench configured to retain at least a portion of the antenna at a specified depth from the surface of the header assembly when the antenna is positioned within the trench; and a silicone material configured to fill the trench when the antenna is positioned within the trench, the silicone material configured to retain the antenna and isolate the antenna from tissue of the patient.

13. The apparatus of claim 12, comprising the implantable medical device, including: the housing including the electronic circuit configured for radio frequency communication; the header assembly, coupled to the housing; and the antenna.

14. The apparatus of claim 13, further comprising an implantable lead assembly; and wherein the header is configured to provide one or more electrical interconnections between one or more conductors included as a portion of the implantable lead and the electronic circuit.

15. A method, comprising: forming an antenna configured to be coupled to an electronic circuit within a housing of an implantable medical device, the electronic circuit configured for radio frequency communication using the antenna; and locating the antenna within a dielectric material comprising one or more of polytetrafluoroethylene, expanded polytetrafluoroethylene, polyetheretherketone, or a thermoplastic polyurethane, the dielectric material formed to provide a header assembly configured to provide an electrical connection for a lead extending away from the header assembly and to isolate the antenna from tissue of a patient when the header assembly is implanted in the patient, and the dielectric material comprising a trench configured to retain at least a portion of the antenna at a specified depth from the surface of the header assembly when the antenna is positioned within the trench; and filling the trench with a silicone material configured to retain the antenna and isolate the antenna from tissue of the patient.

* * * * *